(12) United States Patent
Hess et al.

(10) Patent No.: US 6,444,836 B1
(45) Date of Patent: Sep. 3, 2002

(54) PROCESS FOR THE PREPARATION OF PHOSPHITES

(75) Inventors: Kief Hess, Morgantown, WV (US); James A. Mahood, Evansville, IN (US); Steve Marcus, Morgantown; Charles E. White, Jr., Arthurdale, both of WV (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/863,958

(22) Filed: May 23, 2001

(51) Int. Cl.[7] .................................................. C07F 9/02
(52) U.S. Cl. ......................................................... 558/95
(58) Field of Search ............................................ 558/95

(56) References Cited

U.S. PATENT DOCUMENTS 5,532,401 A     7/1996   Stevenson et al.

*Primary Examiner*—T. A. Solola
*Assistant Examiner*—Joseph Murray

(57) ABSTRACT

A process for manufacturing organic phosphites of at least 95.5 wt. % purity, said process comprising: reacting a hydroxyl-containing compound with a phosphorous compound, and desorbing residual hydroxyl-containing compound in the reaction product in a desorbing column employing an inert gas as a desorbing agent.

14 Claims, No Drawings

PROCESS FOR THE PREPARATION OF PHOSPHITES

FIELD OF THE INVENTION

The present invention is directed to a process for the preparation of organic phosphites, specifically for improving the purity of organic phosphites.

BACKGROUND OF THE INVENTION

Organic phosphites are typically prepared from reactions between phosphorous compounds, e.g., phosphorous trihalides, and an excess amount of appropriate hydroxy compounds. Examples of the hydroxy-substituted aromatic compounds used in the reaction include nonylphenol, dodecylphenol, 2-t-butylphenol, 2,4-di-t-butylphenol, 2-(1, 1-dimethylpropyl) phenol, 2,4-di-t-amylphenol, 2-t-octylphenol, 2,4 di-t-octylphenol, and the like. The reaction is commonly carried out in the presence of a solvent and/or a hydrogen halide acceptor to increase the rate of reaction, e.g., amines such as t-butylamine, t-pentylamine, t-hexylamine, t-octylamine, di-t-butylamine, di-t-pentylamine, di-t-hexyamine, di-t-octylamine, tripropylamine, tributylamine, trimethylamine, triethylamine, N,N-dimethylaniline, N,N-diethylaniline, Hunig base or N,N-dimethyl-aniline and the like.

It is known that the presence of excess/unreacted hydroxy compounds and solvents such as heptane or amines in the organic phosphite product may negatively affect the product quality, e.g., color discoloration. U.S. Pat. No. 5,532,401 discloses a process to remove excess nonylphenyl from the synthesis of tris(nonylphenyl)phosphite using vacuum thin film distillation, i.e., at vacuum levels of about 1–10 mm Hg and temperatures of about 100–350°C.

There is still a need for an improved process for the production of organic phosphites and for improving the purity of organic phosphites.

SUMMARY OF THE INVENTION

The invention relates to a process for manufacturing organic phosphites comprising: reacting a hydroxyl-containing compound with a phosphorous compound in the presence of an amine acid acceptor and desorbing residual hydroxyl-containing compound in the reaction product in a desorbing column employing an inert gas as a desorbing agent.

The invention also relates to a process to purify organic phosphites containing residual hydroxyl-containing compounds by desorbing the residual hydroxyl-containing compound in the reaction product in a desorbing column employing an inert gas as a desorbing agent.

DETAILED DESCRIPTION OF THE INVENTION

Organic phosphites are typically produced by reacting a phosphorous compound with hydroxyl-containing compounds wherein the halides are displaced by the hydroxyl-containing compounds. The organic phosphites of the present invention include phosphonites of the formulae:

or

where each R is independently selected from alkyl, aryl, alkaryl, aralkyl and substituted alkyl, aryl, alkaaryl and arakyl groups. Examples of organic phosphites include triphenyl phosphite, tris(2,5-di-tert-butylphenyl)phosphite, tris(2-tert-butylphenyl)phosphite, tris(2-phenylphenyl) phosphite, tris(2-(1,1-dimethylpropyl)phenyl)phosphite, tris (2-cyclohexylphenyl)phosphite, tris(2-tert-butyl-4-phenylphenyl)phosphite, tris(2-tert-butyl-4-methylphenyl) phosphite, tris(2,4-di-tert-amylphenyl)phosphite and tris(2, 4-di-tertbutylphenyl)phosphite.

1. Reaction to produce organic phosphites. In one embodiment of the invention, organic phosphites are typically produced by reacting a phosphorous halide with hydroxyl-containing compounds wherein the halides are displaced by the hydroxyl-containing compounds. In another embodiment of the invention, organic phosphites are produced from reactions between di-substituted phosphites and hydroxyl-containing compounds wherein the halogen group is displaced by the hydroxyl-containing compounds. In yet a third embodiment, organic phosphites are disphosphites based upon pentaerythritol and prepared from the reaction of pentaerythritol, phosphorous trihalide, and a hydroxyl-containing compound.

Reactant 1—phosphorous compounds. In embodiments wherein phosphorous halides are used, examples of the halide compounds include chlorine, fluorine, bromine, iodine and mixtures thereof. In one embodiment, the halide compound is phosphorous trichloride. In another embodiment, phosphorous tribromide is used.

In embodiments wherein di-substituted phosphites are used, the di-substituted phosphite is a di-substituted phosphorohalidite of the general formula:

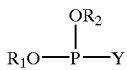

wherein each of R1 and R2 are independently a $C_{1-20}$ alkyl, aryl, or alkaryl moiety and Y is a halogen. In another embodiment, R1 and R2 are interconnected (i.e., the residual of a diol) such that the di-substituted phosphite is a cyclic phosphite. An example is 2-butyl-2-ethyl-1,3-propanediol-monochlorophosphite.

Reactant 2—phenolic compounds. Examples of the hydroxyl-containing compounds in the present invention include but not limited to 2-t-butylphenol, 2,4-di-t-butylphenol, 2-(1,1-dimethylpropyl) phenol, 2,4-di-t-amylphenol, 2-t-octylphenol, 2,4 di-t-octylphenol, 2-t-nonylphenol, 2-t-dodecyl-phenol, 2-(dimethylbenzyl) phenol, and dodecylphenol. In one embodiment, nonylphenol is used.

Optional acid acceptors for increasing the conversion rate. The reaction to prepare organic phosphites is typically promoted, for example, by the use of additional acid acceptors or dehydrohalogenation agents well-known in the art, including amines, pyridines, pyrrolidines, amides, an aqueous alkalide material, or a hydroxide of alkaline metal or alkaline earth metal.

The amines may be primary amine, secondary amine, and tertiary amine commonly used in the art. Examples of the amines include t-butylamine, t-pentylamine, t-hexylamine, t-octylamine, di-t-butylamine, di-t-pentylamine, di-t-hexyamine, di-t-octylamine, tripropylamine, tributylamine, trimethylamine, triethylamine, N,N-dimethylaniline, N,N-diethylaniline, Hunig base or N,N-dimethyl-aniline and the like. In one embodiment, tripropylamine is used as the dehydrohalogenation agent.

Optional organic solvent. In one embodiment of the invention, an organic solvent is used. The organic solvent may be any solvent that does not inhibit the reaction, and is not specifically limited. Examples thereof include aromatic hydrocarbon, aliphatic hydrocarbon, oxygen-containing hydrocarbon, halogenated hydrocarbon and the like. Examples of solvents include heptane, benzene, toluene, xylene, methyl ethyl ketone, acetone and the like. In one embodiment, heptane is used.

2. Preparation of the organic phosphites. The reaction to prepare organic phosphites is performed in devices known to be suitable for the purpose. In general, the hydroxyl-containing compound is placed, optionally together with a solvent, into a reaction vessel. The phosphorous compound is then added, and after addition of at least an optional acid acceptor, the reaction mixture is stirred until the reaction is complete. Stirring is preferably carried out with heating of up to about 200° C. in order to accelerate the reaction. After the reaction has reached equilibrium, any optional solvent used in the reaction may be removed by flash distillation.

3. Purification of organic phosphite end-product. As noted before that there can be an excess amount of phenolic compounds including unreacted phenols plus a small amount of solvents left in the product stream, collectively called "residual phenol." Applicants have found that the excess phenol can be removed in a simple separation step at about atmospheric pressure and relatively low temperature using standard operational apparatuses such stripping type columns, for purified organic phosphites having less than 0.5 wt. percent phenolic compounds.

In the next purification stage of the process, the residual phenol is removed in the presence of an inert/non-reactive gas and surface enhancer such as packing in a column. Examples of non-reactive gas include nitrogen, hydrogen, argon, and carbon dioxide. The column pressure is maintained at about atmospheric pressure. The column temperature is maintained in a range of about 100° C. to about 300° C.

In one embodiment of the invention, the column is maintained at about 150–200° C. via the use of hot oil circulating in the jacket of the column.

In another embodiment of the invention, the incoming non-reactive gas is pre-heated to a temperature of about 150–200° C. before scrubbing.

In one embodiment of the invention, the feed organic phosphite stream to be scrubbed is applied to the top of the column, while a controlled nitrogen gas feed flows in counter-current thereto through the packing bed of the desorber from bottom to top of the column. The descending liquid stream being rich in residual phenols countercurrently contacts the ascending heated nitrogen stream and the dissolved residual phenols are extracted from the organic phosphite stream by the heated nitrogen as vapors. The inert gas and desorbed phenol stream exits the top of the column and passes by a condenser where it is cooled down to about 50° C. The purified organic phosphites are withdrawn at the bottom of the desorber.

In yet another embodiment of the invention, the purified organic phosphite stream withdrawn from the desorber is used as a feed stream to yet another desorber connected in series for further removal of any residual phenols from the organic phosphites to obtain maximum purity in the end-product of less than 0.1 wt. % impurities.

The invention is further illustrated by the following examples. The examples are not, however, to be construed as limiting in anyway.

EXAMPLE 1

A vertical, glass-jacketed column with an inner diameter of 2.7 cm. and a height of 50 cm and filled 43 cm high with glass beads of 3 mm. in diameter is used as the desorber. A glass frit is installed at the bottom of the column for fine disbursement of the nitrogen feed. A nitrogen flow (controlled by a rotometer installed prior to the desorber and maintained at 0.1 SCFM) is fed to the bottom of the desorber. Hot oil maintained at about 175° C. is recirculated through the jacket of the desorber. A water-cooled condenser and distillate collection pot is installed at the outlet of the desorber. Organic phosphite liquid feed stream is manually added to the desorber using a volumetric flask and stopcock setup for a liquid volume in the desorber of about 60 ml. The "purified" product stream is manually drained from the desorber using a stainless steel ball valve and visual level verification in the desorber.

The following table illustrates measured residual phenolic content in the purified product stream for a feed stream composition of approximately 81% Trisnonylphenyl Phosphite (TNPP) and 19% nonylphenol at various feed rate:

| Feed rate (ml/min) | % residual nonylphenol in TNPP |
|---|---|
| 3.9 | 16.3 |
| 3.5 | 9.8 |
| 1.8 | 0.8 |
| 0.5 | 0.4 |

EXAMPLE 2

The same conditions as example 1 except that the column temperature is kept at about 225–240° C. (via the hot oil jacket) and the nitrogen feed stream is pre-heated to about 180–200° C. for a purified TNPP product containing less than 0.2 wt. % nonylphenol with a feed stream of 0.5 ml/min.

EXAMPLE 3

The same conditions as in example 1, except that the outlet stream from the bottom of the desorber is fed through a second desorber in series to further reduce the concentration of residual phenols to significantly less than 0.2 wt. %.

EXAMPLE 4

The same as in example 1, except that the feed stream comprises a mixture of about 20 wt. % 2,4-ditert-butyl phenol (DTBP) and 80 wt % of tris(2,4-di-t-butylphenyl) phosphite for a purified phosphite product containing less than 0.2 wt. % DTBP with a feed stream of 0.5 ml/min.

EXAMPLE 5

A vertical, glass-jacketed column with an inner diameter of 4 cm. and a height of 33 cm and filled about ⅘ high with glass beads of 3 mm. in diameter is used as the desorber. A glass frit is installed at the bottom of the column for fine disbursement of the nitrogen feed. A nitrogen flow (controlled by a rotometer installed prior to the desorber and maintained at 1400 ml/min) is fed to the bottom of the desorber. Hot oil maintained is recirculated through the jacket of the desorber to keep the desorber temperature at about 180° C. A water-cooled condenser and distillate collection pot is installed at the outlet of the desorber. Organic phosphite liquid feed containing about 78% triphenyl phosphite ("TPP") and 22% phenol is fed to the desorber at a rate of about 1.9 mil /min. The "purified" product stream is manually drained from the desorber. The "purified" TPP product stream contains a minimal phenol level of about 0.02%.

EXAMPLE 6

The same as in example 5, except that the nitrogen feed stream is lowered to about 200 mil/min with the concentration of residual phenols being reduced to about 4.3 wt. %.

EXAMPLE 7

The same as in example 5, except that the desorber temperature is maintained at a lower temperature of about 120° C., with the resulting residual phenol concentration in the "purified" TPP product stream of about 8.35%.

Having described the invention, that which is claimed is:

1. A process for manufacturing organic phosphites comprising:
   a) reacting a hydroxyl-containing compound with a phosphorous compound;
   b) desorbing residual hydroxyl-containing compound in the reaction product in a desorbing column employing an inert gas as a desorbing agent;
   wherein:
      an effluent stream from the desorbing column is about at least 99.5 wt. % pure organic phosphites, and
      wherein said hydroxyl-containing compound is a phenolic compound, said phosphorous compound is a phosphorous halide, and said organic phosphites are selected from organic phosphites of the formula:

$$(RO)_2PR\text{—}R \quad \text{(I)}$$

or $$P\text{—}(OR)_3 \quad \text{(II)}$$

where each R is independently selected from alkyl, aryl, alkaryl, aralkyl and substituted alkyl, aryl, alkaaryl and arakyl groups.

2. The process of claim 1, wherein said desorbing agent comprises nitrogen.

3. The process of claim 1, wherein the desorbing column operates at about atmospheric pressure.

4. The process of claim 3, wherein the desorbing column operates at about 100 to 300° C.

5. The process of claim 4, wherein the desorbing column operates at about 150 to 200° C.

6. The process of claim 1, wherein said inert gas is pre-heated to a temperature of about 150–200° C. prior to being fed to the desorbing column.

7. An improved process for purifying organic phosphites by removing residual hydroxy-containing compounds and organic solvents from said phosphites, said process comprising feeding said organic phosphites to a desorbing column employing an inert gas as a desorbing agent, wherein said inert gas desorbs said residual hydroxy-containing compounds and organic solvents from said phosphites for an end product of at least 99.5 wt. % pure organic phosphites, and wherein
   a) said organic phosphites are selected from organic phosphites of the formula:

$$(RO)_2P\text{—}R \quad \text{(I)}$$

or $$P\text{—}(OR)_3 \quad \text{(II)}$$

where each R is independently selected from alkyl, aryl, alkaryl, aralkyl and substituted alkyl, aryl, alkaaryl and arakyl groups;
   b) said hydroxy-containing compounds are phenolic compounds.

8. The process of claim 6, wherein said desorbing column is maintained at a temperature of about 100 to 300° C.

9. The process of claim 7, wherein said inert gas is pre-heated to a temperature of about 150–200° C. prior to being fed to the desorbing column.

10. The process of claim 6, wherein said desorbing column is maintained at a temperature of about 150 to 200° C.

11. The process of claim 1, wherein said organic phosphites are selected from the group consisting of: triphenyl phosphite, tris(2,5-di-tert-butylphenyl)phosphite, tris(2-tert-butylphenyl)phosphite, tris(2-phenylphenyl)phosphite, tris(2-(1,1-dimethylpropyl)phenyl)phosphite, tris(2-cyclohexylphenyl)phosphite, tris(2-tert-butyl-4-phenylphenyl)phosphite, tris(2-tert-butyl-4-methylphenyl) phosphite, tris(2,4-di-tert-amylphenyl)phosphite, and tris(2,4-di-tertbutylphenyl)phosphite.

12. The process of claim 1, wherein said phosphorous halide comprises a halide selected from the group consisting of chlorine, fluorine, bromine, and iodine.

13. The process of claim 1, wherein said phenolic compound is selected from the group consisting of 2-t-butylphenol, 2,4-di-t-butylphenol, 2-(1,1-dimethylpropyl)phenol, 2,4-di-t-amylphenol, 2-t-octylphenol, 2,4 di-t-octylphenol, 2-t-nonylphenol, 2-t-dodecylphenol, 2-(dimethylbenzyl)phenol, dodecylphenol, and nonylphenol.

14. The process of claim 1, wherein said organic phosphites are cyclic phosphites.

* * * * *